United States Patent
Everett et al.

(10) Patent No.: US 9,329,146 B2
(45) Date of Patent: May 3, 2016

(54) TRANSIENT ELECTROMAGNETIC GEOPHYSICS SYSTEM WITH COOPERATIVE SOURCE(S)

(71) Applicant: Texas A&M University System, College Station, TX (US)

(72) Inventors: Mark Everett, College Station, TX (US); Alfonso Benavides Iglesias, College Station, TX (US)

( * ) Notice: Subject to any disclaimer, the term of this patent is extended or adjusted under 35 U.S.C. 154(b) by 367 days.

(21) Appl. No.: 13/758,859

(22) Filed: Feb. 4, 2013

(65) Prior Publication Data

US 2014/0218017 A1 Aug. 7, 2014

Related U.S. Application Data (60) Provisional application No. 61/591,524, filed on Jan. 27, 2012.

(51) Int. Cl.
   *G01V 3/15* (2006.01)
   *G01R 33/341* (2006.01)
   *G01N 27/02* (2006.01)

(52) U.S. Cl.
   CPC .................................. *G01N 27/025* (2013.01)

(58) Field of Classification Search
   CPC ....... G01V 3/104; G01V 3/15; G01N 24/084; G01N 27/622; G01N 33/0057; G01N 27/025; G01N 27/72; G01R 33/341; G01R 33/422
   USPC .......... 324/232, 67, 228, 239, 225, 326, 537; 342/22, 83, 102
   See application file for complete search history.

(56) References Cited

U.S. PATENT DOCUMENTS

| | | | | |
|---|---|---|---|---|
| 7,355,409 B2* | 4/2008 | Larsen | | 324/326 |
| 7,701,204 B2* | 4/2010 | Westersten | | 324/228 |
| 8,450,997 B2* | 5/2013 | Silverman | | 324/207.15 |
| 2003/0052684 A1* | 3/2003 | Nelson et al. | | 324/329 |
| 2008/0018333 A1* | 1/2008 | Zhu | | 324/301 |
| 2008/0297158 A1* | 12/2008 | Heger et al. | | 324/326 |
| 2010/0213770 A1* | 8/2010 | Kikuchi | | 307/104 |
| 2011/0087628 A1* | 4/2011 | Bennani | | 706/25 |
| 2011/0184681 A1* | 7/2011 | Augustine et al. | | 702/75 |
| 2012/0280679 A1* | 11/2012 | Shelton | | 324/207.16 |

OTHER PUBLICATIONS

Dr. Mark E. Everett and Alfonso Benavides Iglesias, Experimental Time-Domain Controlled Source Electromagnetic Induction for Highly Conductive Targets Detection and Discrimination. (May 2007).*

* cited by examiner

*Primary Examiner* — Tung X Nguyen
*Assistant Examiner* — Neel Shah (57) ABSTRACT

A cooperative source electromagnetic induction (EMI) device includes: a transmitter configured to generate a time-varying primary magnetic field in the vicinity of a target object, which magnetic field inductively couples with the target object to generate a target object secondary magnetic field; and a cooperative source to which the primary magnetic field is also inductively coupled, generating one or more respective cooperative source secondary magnetic fields. The target object and the cooperative source are inductively coupled via the target object secondary magnetic field and the cooperative source secondary magnetic field. The device includes a receiver configured to measure a composite inductive response, which comprises the inductive coupling of the target object and the cooperative source. A data processor executes statistical classifier software to interpret a signature of the target object based upon the measured composite inductive response and identify the target object from the interpreted signature.

20 Claims, 10 Drawing Sheets

TRANSIENT ELECTROMAGNETIC GEOPHYSICS SYSTEM WITH COOPERATIVE SOURCE(S)

PRIORITY

This present application claims priority from U.S. Provisional Application No. 61/591,524, filed on Jan. 27, 2012. The entire content of that application is incorporated herein by reference.

TECHNICAL FIELD

This disclosure relates generally to the field of electromagnetic induction (EMI) sensing systems for the detection of electrically conductive target objects. More specifically, but not by way of limitation, this disclosure relates to improved systems and methods for acquiring and interpreting electromagnetic responses that allow metallic target objects to be classified with greater precision.

DESCRIPTION OF RELATED ART

Existing electromagnetic induction (EMI) sensing systems (e.g., metal detectors) are commonly used in a variety of applications. Just by way of example, such sensing systems may be utilized in airport security, in geophysics to detect buried unexploded ordnance or mineral deposits, in civil engineering to identify the presence of metal reinforcing materials within building walls and foundations, and in personal pursuits (i.e., as a hobby) to identify buried metal objects.

While existing EMI sensing systems are well-suited to identify the presence of a conductive target object, they are not well-suited to determine key properties (e.g. shape, size, and orientation) of the target object that has been detected. That is, existing systems are ill-equipped to accurately discriminate between target objects that are of particular interest to a user of the system and those that are not.

SUMMARY

Disclosed are a system, device, and method for classifying (i.e., enabling identification of a target's electromagnetic transients as belonging to a particular group of target transients) and discriminating (i.e., correctly distinguishing from the identification of a target's electromagnetic transients whether the target is of interest or is not of interest) an unknown target object utilizing a cooperative source within a cooperative source electromagnetic induction (EMI) generating and sensing system. According to one aspect, the device includes: a transmitter configured to generate a time-varying primary magnetic field in the vicinity of the target object, which time-varying primary magnetic field inductively couples with the target object to generate a target object secondary magnetic field; and at least one cooperative source to which the primary magnetic field is also inductively coupled, generating one or more respective cooperative source secondary magnetic fields. The target object and the at least one cooperative source are inductively coupled via the target object secondary magnetic field and the one or more cooperative source secondary magnetic fields. The device further includes a receiver configured to measure a composite inductive response, which comprises a measurement of the inductive coupling of the target object and the one or more cooperative sources. According to one embodiment, the device further includes and/or is communicatively coupled to a data processor executing statistical classifier software that is configured for: interpreting a signature of the target object based upon the measured composite inductive response; and identifying the target object from the interpreted signature.

According to another aspect, the method includes: generating a time-varying primary magnetic field in the vicinity of the target object, which primary magnetic field inductively couples with the target object to induce a target object secondary magnetic field; positioning at least one cooperative source in the vicinity of the target object and the transmitter, where an inductive coupling of the primary magnetic field with the at least one cooperative source generates a cooperative source secondary magnetic field. The target object and the cooperative source are inductively coupled via the target object secondary magnetic field and the cooperative source secondary magnetic field. The method further includes measuring, with a receiver, a composite inductive response that comprises a measurement of the inductive coupling of the target object and the cooperative source. In one embodiment, the generating of the time-varying primary magnetic field includes configuring a transmitter of an electromagnetic induction (EMI) sensing device to perform the generating. Also, the receiver is a component of the EMI sensing device.

The method further includes: measuring a background (subsurface natural materials, including soil, rocks, and fluids within) inductive response, a primary target inductive response, and a cooperative source inductive response; removing the background inductive response, the primary target inductive response, and the cooperative source inductive response from the composite inductive response to yield the measurement of the inductive coupling transient of the target object and the cooperative source.

In one embodiment the method further includes: collecting a plurality of measurements of the composite inductive response, with the receiver, for a plurality of cooperative source positions and (b) a plurality of orientations of at least one cooperative source; generating a target object signature from the collected plurality of measurements; and interpreting the target object signature utilizing a statistical classification algorithm. The statistical classification algorithm utilizes one or more of (a) self-organizing maps and/or (b) merge self-organizing maps. In at least one embodiment, the at least one cooperative source is a cooperative source array comprising a plurality of cooperative sources.

The above summary contains simplifications, generalizations and omissions of detail and is not intended as a comprehensive description of the claimed subject matter but, rather, is intended to provide a brief overview of some of the functionality associated therewith. Other systems, methods, functionality, features and advantages of the claimed subject matter will be or will become apparent to one with skill in the art upon examination of the following figures and detailed written description.

BRIEF DESCRIPTION OF THE DRAWINGS

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein, in which.

DETAILED DESCRIPTION

The present disclosure provides a system and/or device and method for classifying (i.e., enabling identification of a target's electromagnetic transients as belonging to a particular group of target transients) and discriminating (i.e., correctly distinguishing from the identification of a target's electromagnetic transients whether the target is of interest or is not of interest) an unknown target object utilizing a cooperative source within a cooperative source electromagnetic induction (EMI) generating and sensing system. The following provides a detailed description for carrying out embodiments of the disclosure. This description is not to be taken in a limiting sense, but is made merely for the purpose of illustrating the general principles of the example embodiments of the disclosure.

In the following detailed description of exemplary embodiments of the disclosure, specific exemplary embodiments in which the disclosure may be practiced are described in sufficient detail to enable those skilled in the art to practice the disclosed embodiments. For example, specific details such as specific method orders, structures, elements, and connections have been presented herein. However, it is to be understood that the specific details presented need not be utilized to practice embodiments of the present disclosure. It is also to be understood that other embodiments may be utilized and that logical, architectural, programmatic, mechanical, electrical and other changes may be made without departing from general scope of the disclosure. The following detailed description is, therefore, not to be taken in a limiting sense, and the scope of the present disclosure is defined by the appended claims and equivalents thereof.

References within the specification to "one embodiment," "an embodiment," "embodiments", or "one or more embodiments" are intended to indicate that a particular feature, structure, or characteristic described in connection with the embodiment is included in at least one embodiment of the present disclosure. The appearance of such phrases in various places within the specification are not necessarily all referring to the same embodiment, nor are separate or alternative embodiments mutually exclusive of other embodiments. Further, various features are described which may be exhibited by some embodiments and not by others. Similarly, various requirements are described which may be requirements for some embodiments but not for other embodiments.

It is understood that the use of specific component, device and/or parameter names and/or corresponding acronyms thereof, such as those of the executing utility, logic, and/or firmware described herein, are for example only and not meant to imply any limitations on the described embodiments. The embodiments may thus be described with different nomenclature and/or terminology utilized to describe the components, devices, parameters, methods and/or functions herein, without limitation. References to any specific protocol or proprietary name in describing one or more elements, features or concepts of the embodiments are provided solely as examples of one implementation, and such references do not limit the extension of the claimed embodiments to embodiments in which different element, feature, protocol, or concept names are utilized. Thus, each term utilized herein is to be given its broadest interpretation given the context in which that term is utilized.

Figure 1:
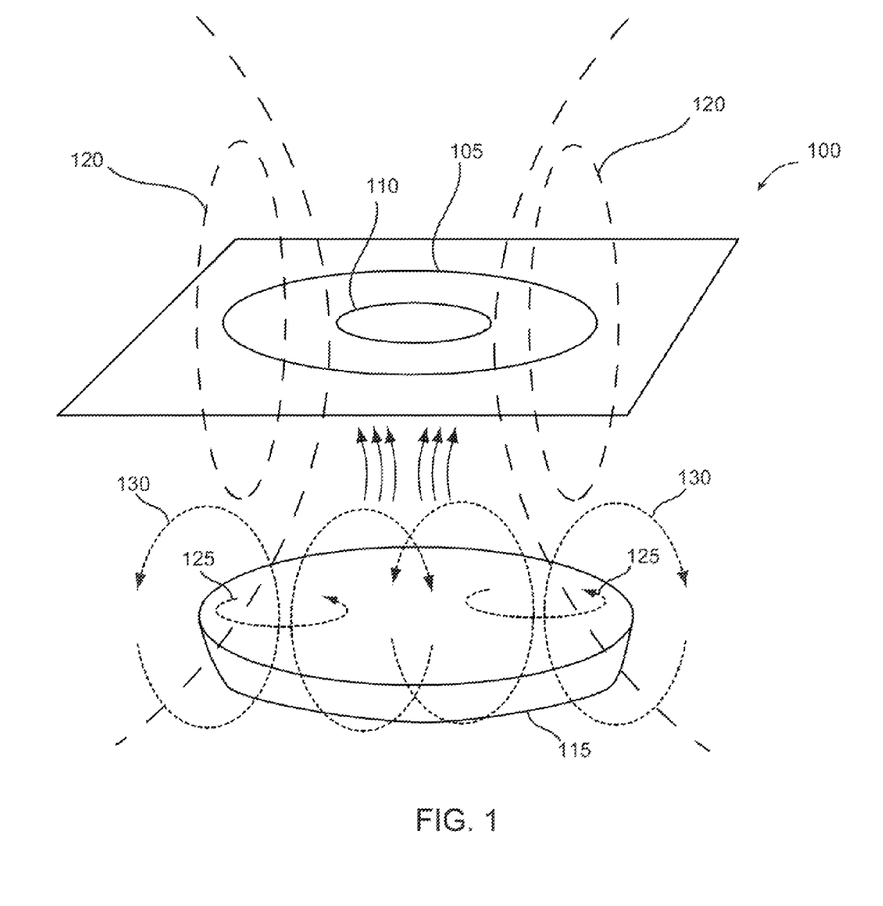
FIG. 1 is a perspective view of an existing electromagnetic induction (EMI) sensing system that utilizes a single transmitter coil and a single receiver coil.

With reference now to the figures wherein like reference numbers denote like parts, FIG. 1 illustrates an example of an EMI sensing system in its most general, scientific form. As introduced above, aspects of the disclosure focus on a system and/or device and method for classifying and discriminating an unknown target object utilizing a cooperative source within an electromagnetic induction (EMI) sensing system. Within the presented description, an EMI system that generates a continuous sinusoidal or any repetitive signal at a certain base frequency (which are usually classed as "frequency-domain" systems) is considered herein to be a time-domain system. Both time-domain and frequency-domain systems are therefore covered by and/or included within the disclosure concepts. As illustrated in FIG. 1, existing EMI sensing systems 100 comprise one transmitting coil 105 through which an alternating or other time-varying current is passed. As the time-varying current passes through the transmitting coil 105, a time-varying electromagnetic field 120 is produced. As is well known in the art, when a conductive material 115 (in this case a target object) is exposed to a changing magnetic field 120, eddy currents 125 are induced in the conductive material 115. These induced eddy currents 125, in turn, produce a secondary magnetic field 130 of their own. One or more receiving coils 110 measures the secondary magnetic field 130 and can therefore detect the presence of a conductive material based on a change in the measured secondary magnetic field.

Figure 2:
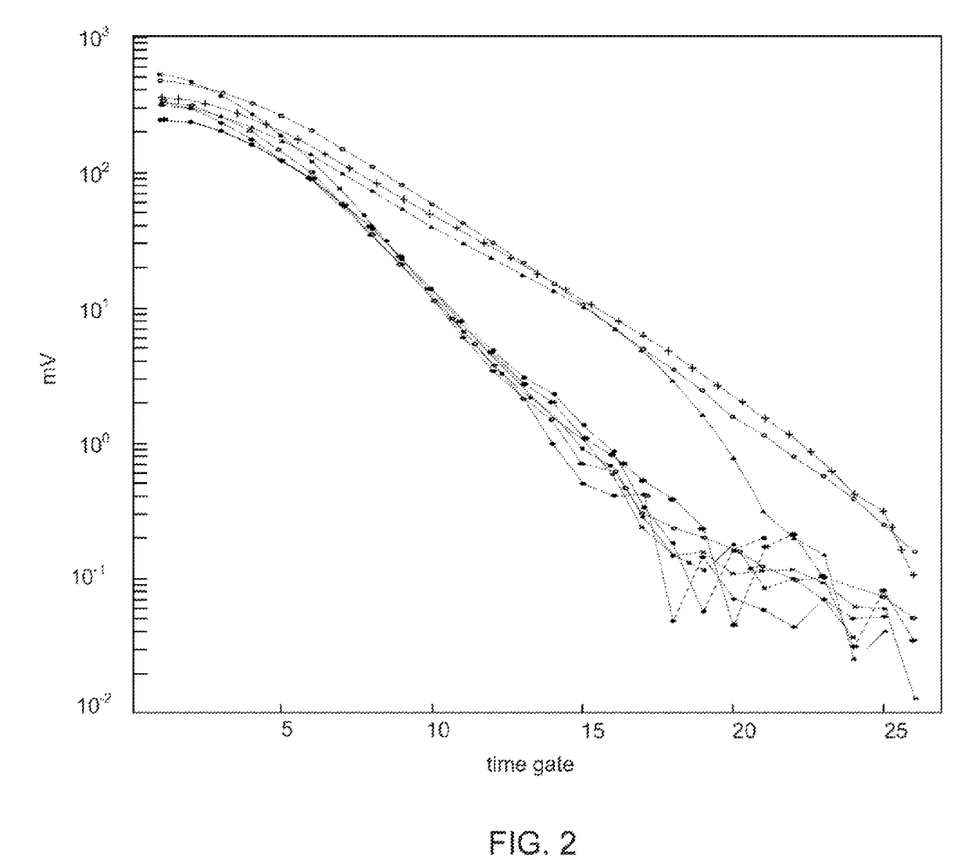
FIG. 2 shows electromagnetic responses of various electrically conductive target objects measured using an existing EMI sensor system that utilizes a single transmitter coil and a single receiver coil.

An existing EMI sensor would produce measurements such as those mapped in FIG. 2. As illustrated in FIG. 2, the electromagnetic responses of each of the objects vary to such a small degree that, with the presence of signal noise, it is difficult to reliably and consistently identify or classify properties of the object detected by the sensor. For example, it is likely that a user of the above EMI sensing system 100 searching for buried unexploded ordnance would misclassify everyday scrap metal as unexploded ordnance (or vice versa) because the target objects may produce similar electromagnetic responses.

One improved classification technique known in the art determines the type of target object by calculating and then comparing its EMI response attributes (e.g., EMI polarizabilities) against those of expected targets. The target attributes are estimated by inverting measured EMI responses using a physics-based forward modeling algorithm. The physics-based forwarding model is based on the presumption of a target EMI polarizability tensor. For example, in the field of unexploded ordnance classification, unexploded ordnance typically has one large principal axis polarizability $\beta_1$ and two smaller, but approximately equal polarizabilities, $\beta_2$ and $\beta_3$. In stark contrast, ordnance fragments, range scrap, and cultural debris generally exhibit three distinct polarizabilities, where $\beta_1 \neq \beta_2 \neq \beta_3$. Thus, a target object of interest may be classified based on these attributes.

Classification becomes even more difficult in rough or densely vegetated terrain, in built-up environments, in the presence of magnetic soils, or in the presence of multiple buried targets with spatially overlapping response signatures. Thus, aspects of the present disclosure provides a new design and methodology to traditional EMI sensing systems that enables more precise classification of objects detected through the use of an EMI sensing system, with a cooperative source. The system and design is referred to herein as a cooperative source EMI generating and sensing system or cooperative source EMI device.

As utilized herein, a cooperative source is an object of known shape, size, composition and orientation. In the described embodiments the cooperative source is assumed to be metal based on the qualities required to generate indicative currents from exposure to the transmitter magnetic fields. Thus, in the described embodiments, the cooperative source comprises a metal object that couples inductively to a time-varying magnetic field. Further, in one or more of the described embodiments, one or more of the at least one cooperative source is a circuit that is configured to be switchable between an open-circuit and a closed-circuit configuration. The cooperative source is placed close to an EMI sensing device when the latter is above a target object of unknown shape, size, burial depth, composition and orientation. The electromagnetic sensing device generally comprises one transmitter coil and at least one receiver coil. A cooperative source is systematically activated at various positions around the target object and an induction response is recorded at each position. Each measurement includes a combination of: (i) the EMI signature of the unknown target; (ii) the EMI signature of the cooperative source; (iii) the EMI signature of the inductive coupling between the unknown target and the cooperative source, and; (iv) the background EMI signature of the soil.

Thus, with the above introduced processes involving the cooperative source, certain auxiliary inductive response measurements are made in order to extract the most useful data from the inductive response measurement. A first auxiliary measurement is made with the target object present but without the cooperative source, a second auxiliary measurement is made nearby with the cooperative source present but without the target object, and a third auxiliary measurement is made nearby with neither the cooperative source nor the target object present. The sum of these auxiliary measurements can then be subtracted from the inductive response measurement that was made with the cooperative source and target object present. The result yields the mutual inductive coupling signal between the cooperative source and target object, which may be used as input to a statistical classification procedure in order to classify the target object.

Figure 3:
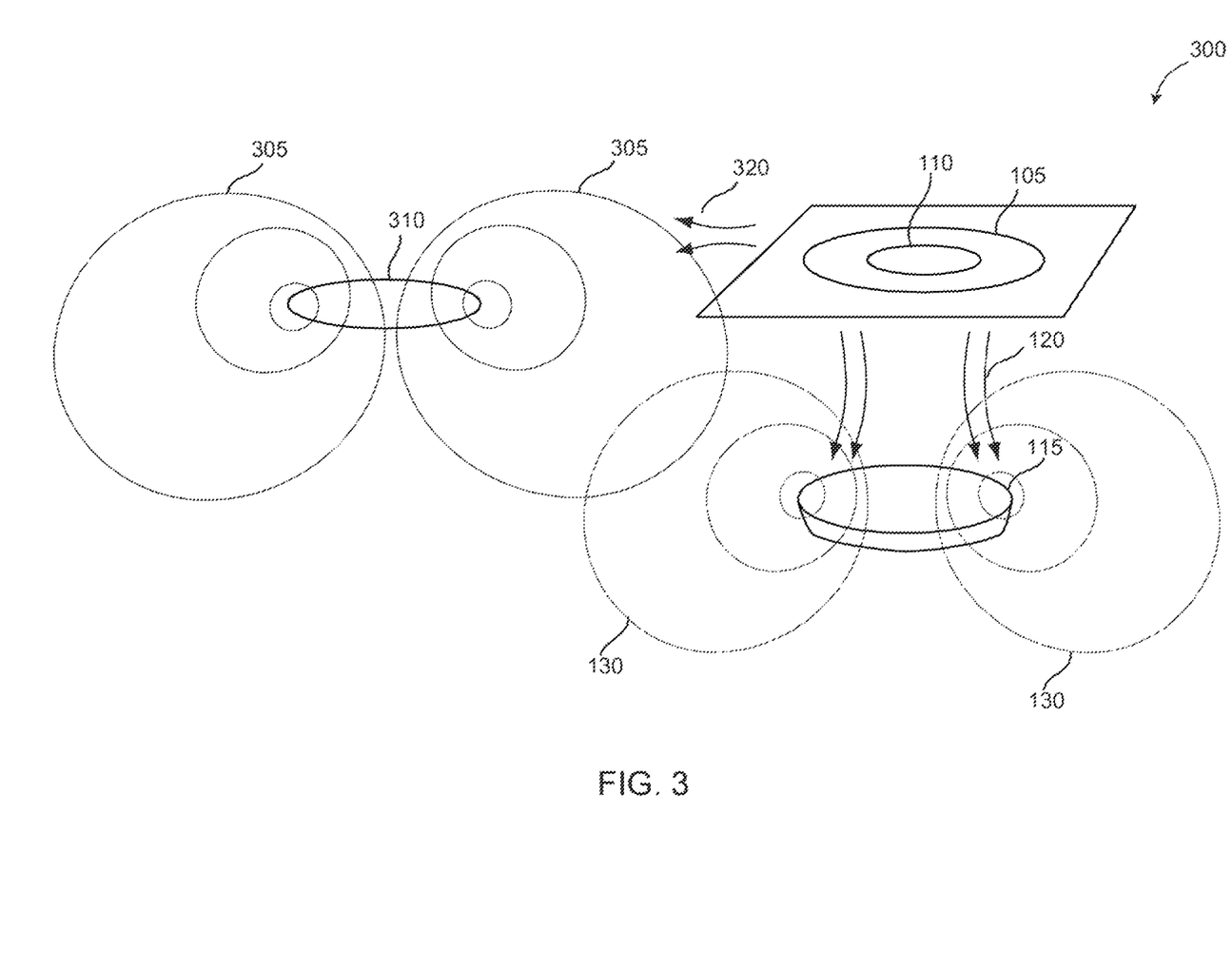
FIG. 3 is a perspective view of the cooperative source system in accordance with an embodiment of the disclosure.
Figure 4A:
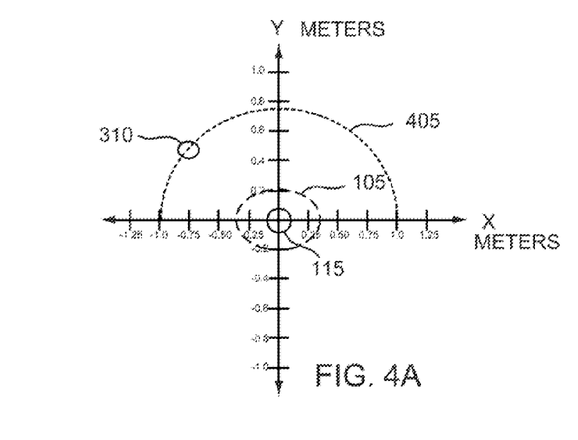
FIGS. 4A-4D are plan views of the cooperative source system to illustrate an embodiment in which a cooperative source is systematically activated at predefined locations in the vicinity of a target object.
Figure 4B:
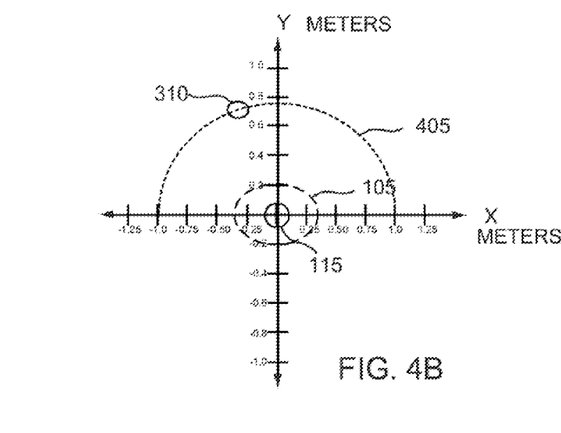
Figure 4C:
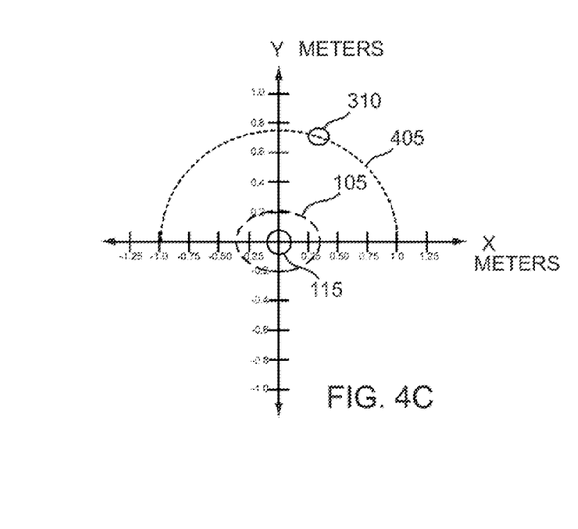
Figure 4D:
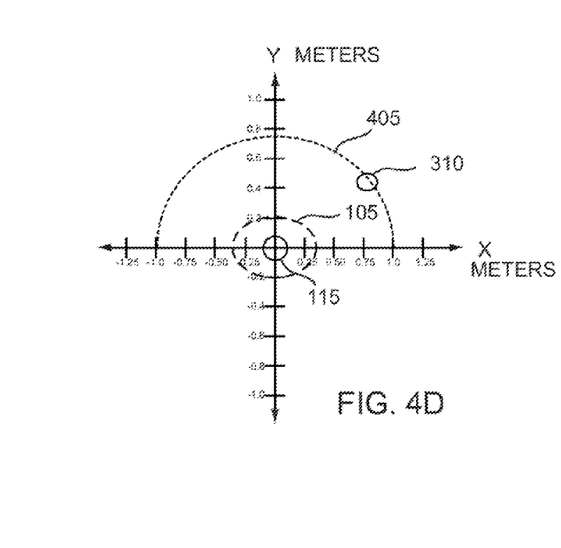

Referring to FIG. 3, in a first embodiment, the cooperative source EMI device 300 consists of a transmitter coil 105, receiver coil 110, and cooperative source 310. The transmitter coil 105 generates a time-varying electromagnetic field 120 in the vicinity of both the target object 115 and the cooperative source 310. The time-varying electromagnetic field 120 induces eddy currents in both the target object 115 and the cooperative source 310 which create secondary electromagnetic fields, 130 and 305, respectively. In this manner, the inductive coupling of the primary magnetic field with both the target object 115 and the cooperative source 310 generates the secondary magnetic fields 130 and 305. The target object's secondary electromagnetic field 130 energizes the cooperative source 310, while the cooperative source secondary electromagnetic field 305 energizes the target object 115. In this manner, the cooperative source 310 and the target object 115 are inductively coupled. In a similar manner, the target object 115 and the receiver coil 110 are inductively coupled. Likewise, the cooperative source 310 and receiver coil 110 are inductively coupled. The receiver coil 110 measures the composite inductive response, i.e., the composite electromagnetic field generated by the combined interactions of the transmitter coil 105, receiver coil 110, cooperative source 310, and target object 115. The composite inductive response is referred to as L|pcs. As one skilled in the art will appreciate, the cooperative source EMI device 300 is not limited to a single transmitter and receiver, but instead may utilize multiple transmitters and/or receivers as well as multiple cooperative sources to achieve results similar in principle to those illustrated by FIG. 3.

Embedded in the L|pcs dataset is the coupling term, L|mi that represents the mutual inductance between the target object 115 and the cooperative source 310. According to one embodiment, this coupling term depends most importantly on the relative geometry of the target object 115 and the cooperative source 310. As the position or orientation of the cooperative source 310 is varied, the relative geometry between the target object 115 and cooperative source 310 varies as well. While this coupling term is captured by the L|pcs dataset, the coupling term must be extracted in order to more precisely classify the target object 115. Accordingly, the following measurements must be made: L|p; L|cs, L|bg. L|p (primary target EMI response) is measured with only the target object 115 present, as illustrated by FIG. 1. L|cs (cooperative source EMI response) is measured in an area away from the influence of the target object 115 with only the cooperative source 310 present. L|bg (background inductance) is measured in the same nearby area (where no target signals are detected) as the L|cs measurement, but without the cooperative source 310 present. L|bg is used to monitor and correct the data for the electromagnetic effects of the geological medium, system noise, and any systematic instrument effects such as the azimuthal variability of the primary field generated by the transmitter coil 105. L|mi measurement is a linear combination of three measurements, as described in the paragraph below. The nomenclature is summarized in the below Table 1.

TABLE 1

Dataset nomenclature.

| Measurement | primary target | cooperative source |
|---|---|---|
| L\|bg | N | N |
| L\|p | Y | N |
| L\|cs | N | Y |
| L\|pcs | Y | Y |
| L\|mi | — | — |

Y = present.
N = absent

To isolate the mutual inductance between the target object 115 and the cooperative source 310, the sum of L|p and L|cs as well as −L|bg are subtracted from L|pcs. This yields L|mi, as shown by the following equation:

$$L|mi = L|pcs - (L|p + L|cs) + L|bg$$

(i.e., mutual coupling=composite−(primary target+cooperative source)+background). The sign of the L|bg term is positive in the above equation in order to remove the background response from L|mi. The final term in the above equation is additive because the second term effectively subtracts the background response twice.

FIGS. 4A-4D present X-Y coordinate maps in plan-view or equivalent, shown on a horizontal plane, centered on a location of a target object 115. Referring to FIGS. 4A-4D, L|pcs is measured as the cooperative source 310 is activated along a series of predetermined locations 405 relative to the target object 115 and L|mi is calculated from each L|pcs measurement. In the illustration, the target object 115, of unknown geometry, is located beneath the transmitting coil 105. The cooperative source 310 is positioned near the transmitting coil 105, at one of the predetermined locations 405. The transmitting coil 105 is energized by a power source (not shown), and as previously described and as illustrated by FIG. 3, the energized transmitting coil 105 generates an inductive coupling between the cooperative source 310 and the target object 115. As the cooperative source 310 is moved through the series of predetermined locations 405, the cooperative source EMI device 300 is activated and L|pcs is measured at each location.

As illustrated in FIGS. 4A-4D, the cooperative source 310 is systematically activated at each of the predetermined locations 405. As the position of the active cooperative source 310 changes, so too does its relative orientation with respect to the target object 115. This change in geometry causes systematic changes in the mutual inductance between the cooperative source 310 and the target object 115, which are captured in the L|pcs measurement. The mutual inductance between the cooperative source 310 and target object 115 is then extracted by applying the L|mi equation. The L|mi dataset yields a target object signature that may be used to classify and discriminate between various target object types and orientations. The orientation of the cooperative source may also be varied in a predetermined sequence at each of the predetermined locations 405. Additionally, it is appreciated that the cooperative source 310 and target object 115 do not need to be azimuthally symmetric, as shown in the illustration. Rather, the cooperative source 310 and/or the target object 115 can be irregular in shape, in one or more implementations.

Figure 5A:
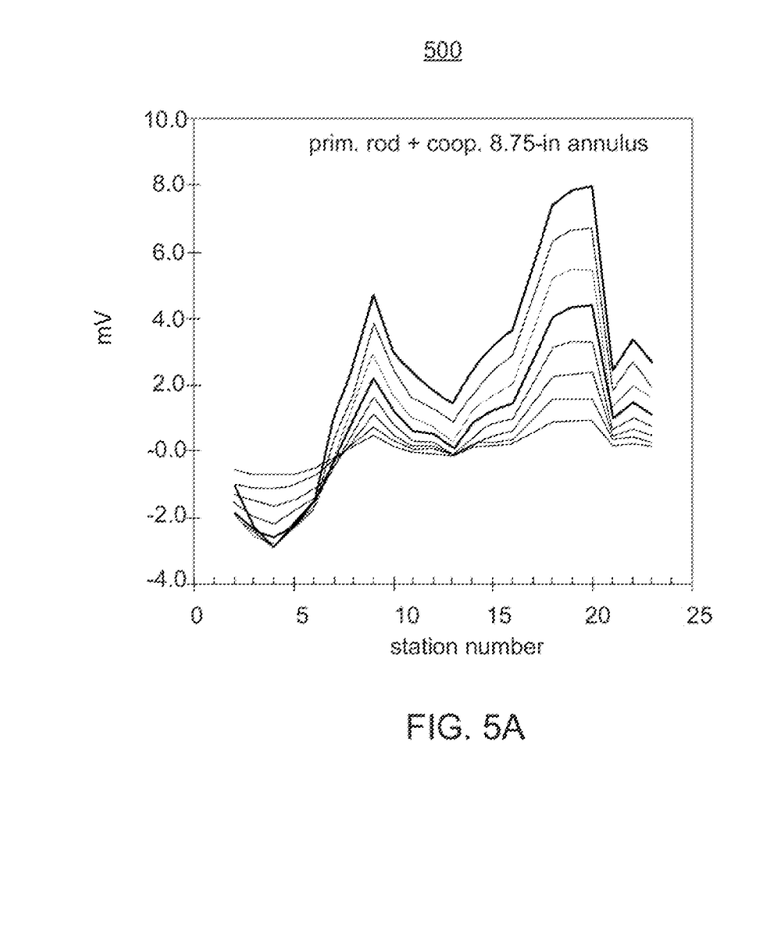
FIGS. 5A-5B illustrate the variation in the mutual electromagnetic coupling between the cooperative source and target object as a function of the cooperative source location for two different target object orientations.
Figure 5B:
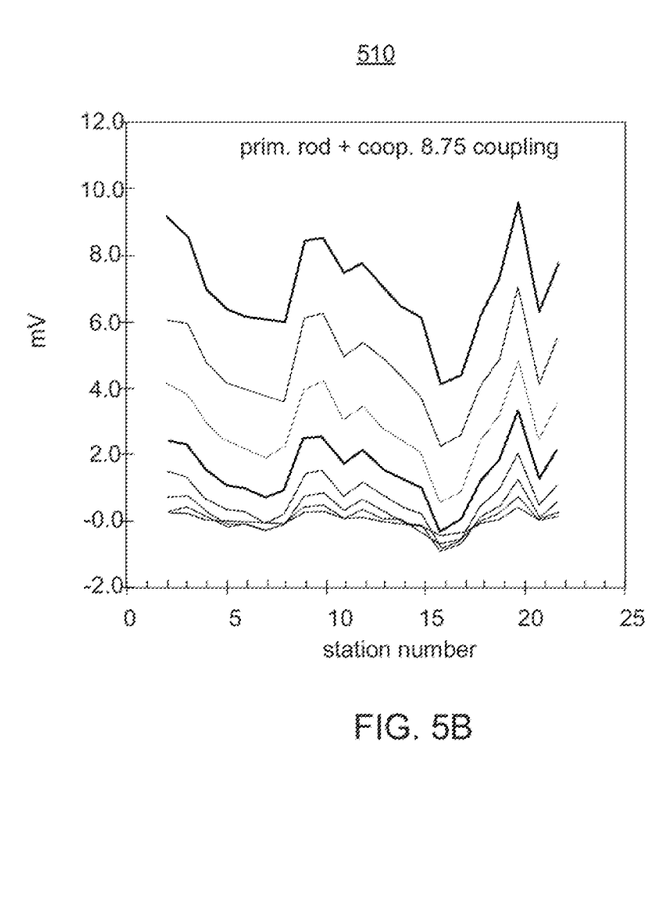

FIGS. 5A and 5B provide graphs 500 and 510, respectively illustrating the variation of the L|pcs signal affected by inductive coupling between the cooperative source 310 and the target object 115 as a function of the cooperative source location. The L|pcs dataset of FIG. 5A was measured using a 20 cm long, 2.5 cm diameter brass rod as the target object 115 and a 22.2 cm diameter thin copper annulus as the cooperative source 310. The brass rod representing the target object 115 was placed in the center of a transmitter coil 105 and the copper annulus representing the cooperative source 310 was laid horizontally on the ground in the vicinity of the target object 115. The graph (or map) illustrates the resulting spatiotemporal L|pcs dataset (the different lines representing measured responses at different time values after shut-off of the transmitter current), with the geological background subtracted using the L|bg measurement. The horizontal axis "station number" refers to the location of the cooperative source 310, numbered sequentially clockwise, similar to the illustrations of FIGS. 4A-4D. The L|pcs data show two characteristic rises which are mainly due to the azimuthal dependence of the primary flux owing to the particular geometry of the transmitter coil 105. The rises in the L|pcs dataset illustrates the necessity to calibrate the EMI responses against the spatial dependence of the primary flux from the transmitter coil 105.

Turning to FIG. 5B, additional L|p and L|cs datasets were acquired. A subtraction of the L|cs response from the L|pcs response removes the contribution produced by the eddy current decay in the cooperative source 310, leaving the signal produced by the target object 115 plus the magnetic coupling between the cooperative source 310 and the target object 115. The resulting profiles after the subtraction just described are shown in FIG. 5B. As illustrated, a receiver voltage maximum is observed between stations 9-14, where the cooperative source is aligned with the principal axis of the brass rod.

The known geometry of the cooperative source 310 permits important information to be acquired about the unknown geometry of the target object 115, as the cooperative source location is varied. For example, the mutual coupling term should be largest when the principal axes of the cooperative source 310 and target object 115 are moved into a parallel alignment and smallest when the two objects are in a perpendicular alignment. Additional information about the target object 115 can be obtained by varying the orientation of the principal axis of the cooperative source 310, or by employing a different cooperative source.

According to one aspect, the geometry of the cooperative source 310 should be chosen such that it is likely to develop strong inductive coupling to the target object 115. Metal annuli, coils (in particular spiral coils or cylindrical coils), and rings are very useful cooperative sources in this regard because they support persistent and vigorous eddy currents with a well-defined decay constant. In contrast, metal spheres, cylinders, blocks, plates, and disks are moderately useful as cooperative sources because their eddy currents rapidly diffuse throughout the distributed metal volume, which results in a broad distribution of decay constants. Elongated cooperative sources such as elliptical rings can be valuable because their mutual coupling to the primary target may be strongly directional. Wire segments and thin rods are generally poor cooperative sources because they have very low inductance and do not support significant eddy current densities.

FIGS. 6A-6D, illustrate the response signatures of various target objects. It should be noted that L|p has not been subtracted in the maps of FIGS. 6A-6D, as subtracting L|p from L|pcs has no effect on the shape of the graphed/mapped L|mi dataset. This is because L|p has no relationship to the azimuth of the cooperative source.

Figure 6A:
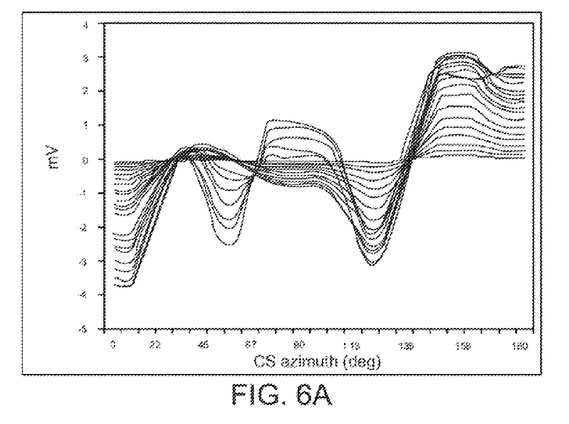
FIG. 6A-6D illustrate response signatures of various target objects using a cooperative source EMI device.
Figure 6B:
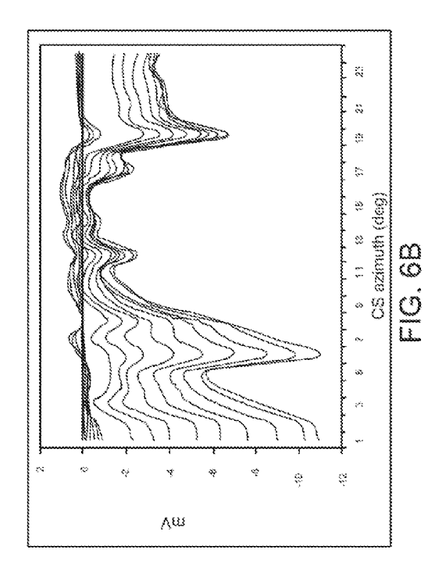
Figure 6C:
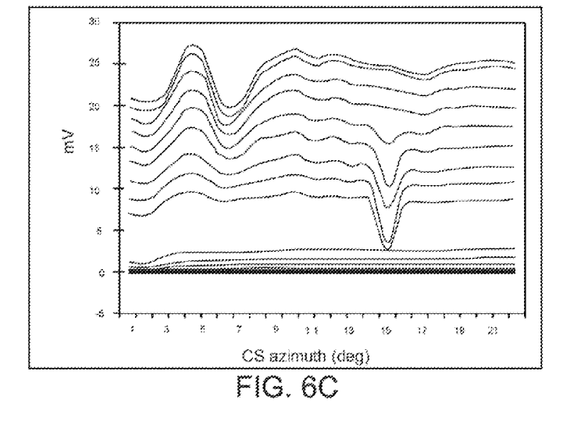
Figure 6D:
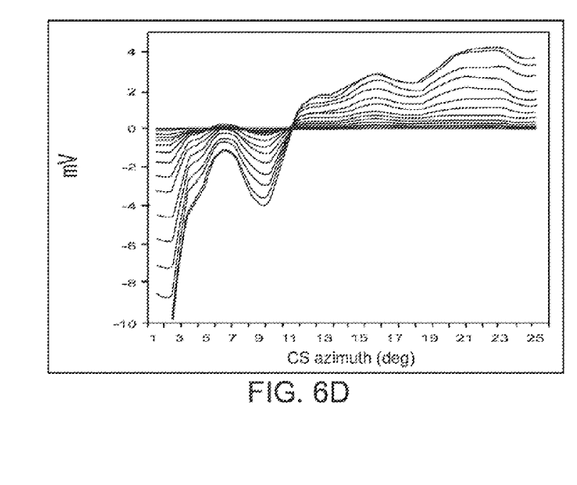

FIG. 6A is an example of results that may be achieved by applying the cooperative source system to an ordnance-shaped target object. FIG. 6B is an example of the results that may be achieved by applying the cooperative source device to an aluminum disk target object. FIG. 6C is an example of the results that may be achieved by applying the cooperative source device to a copper rod target object. FIG. 6D is an example of results that may be achieved by applying the cooperative source device to a brass rod target object. It is clear based upon FIGS. 6A-6D that the response signatures of the different target objects are different from each other and hence allow for more accurate classification and discrimination of target objects than is possible using existing EMI sensing devices. For example, FIG. 2 illustrates the measured responses of various target objects (different lines) as a function of time (x-axis) using an existing EMI sensor. As is illustrated, the similar responses of the various target objects do not allow for the accurate classification and discrimination of the target objects.

Figure 7A:
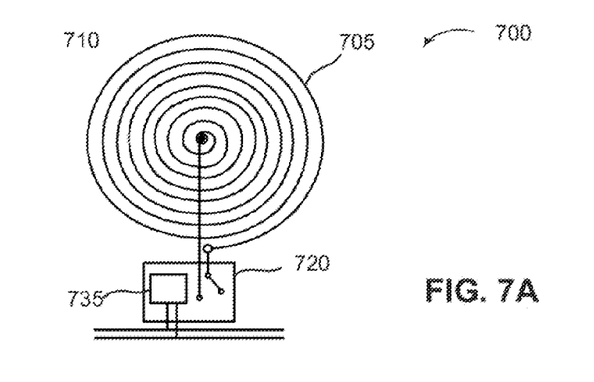
FIG. 7A illustrates a passive cooperative air coil that can be utilized as a cooperative object in one or more embodiments.
Figure 7B:
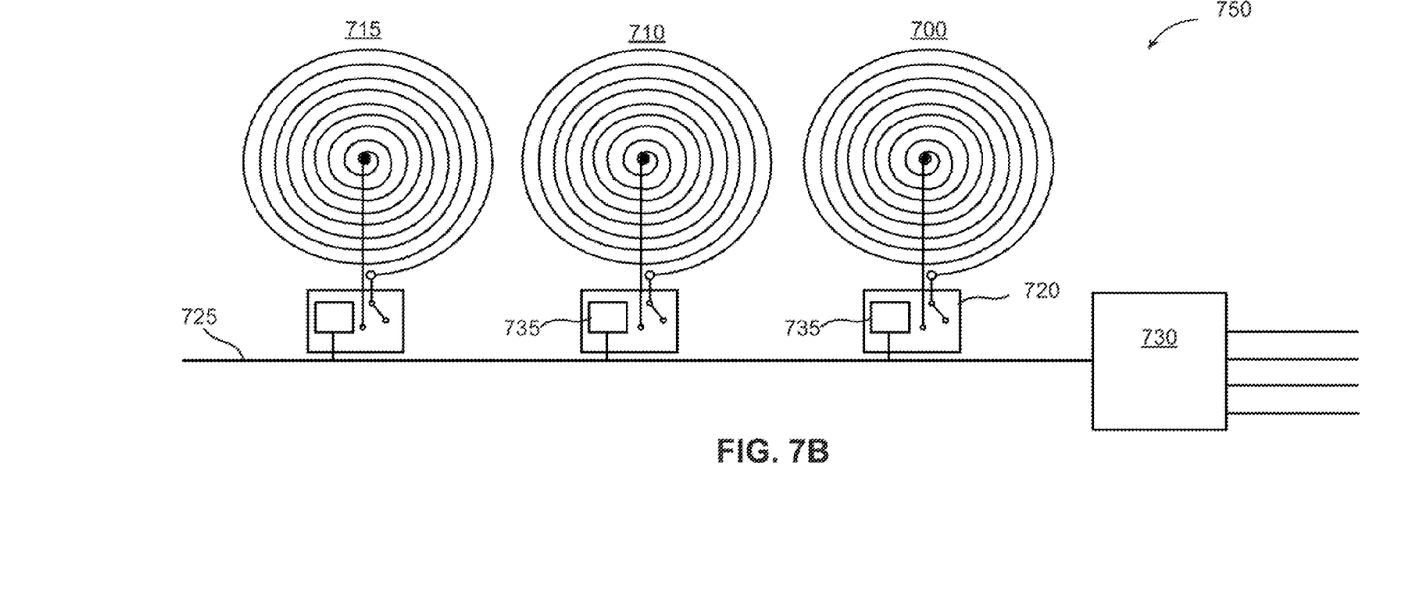
FIG. 7B illustrates a controllable cooperative source array in accordance with an embodiment of the disclosure.

Referring to FIG. 7A, there is illustrated an example cooperative source 700, which is implemented as a circuit that can be controllably opened or closed. The cooperative source 700 is a passive cooperative air-core coil depicted as circular spiral coil 705. The cooperative source 700 can be opened or closed by using a switching circuit 720 located within the cooperative source 700 when a control signal is sent through a communication cable 725. FIG. 7B then illustrates a cooperative source array 750. Cooperative source array 750 is an array of several cooperative sources 700, 710, 715 serially connected via their respective switching circuits 720. Each cooperative source 700, 710, 715 is a passive cooperative air-core coil that can be selectively placed in an open or closed circuit position using a switching circuit 720. As show, the switching circuit 720 includes an open-close control component 735 that is triggered by input received from a main switchbox 730 to which each switching circuit 720 is connected. The main switchbox 730 is in turn controlled by a set of digital lines. Four digital lines are illustrated, allowing for receipt of a 4-bit digital control signal, in one embodiment. The specific number of lines and associated control signal are variable.

According to the described embodiments, the close-loop area of each cooperative source is much greater when the coils are in the closed position (i.e., induced eddy currents can flow through the coil) than when the coils are in the open position. A communication cable 725 connecting array controller 730 to local switch control 735 of each switching circuit 720 allows for the use of control signals to open or close the switching circuits 720. The switching circuit 720 allows for any combination of cooperative sources 700, 710, or 715 to be placed into the open-circuit or closed-circuit mode. The sequential opening and closing of the cooperative sources in a switched cooperative source array is equivalent to moving a single cooperative source sequentially through each of the array locations.

It is further understood that the greater the number of combinations of closed-circuit cooperative sources measured, the more detailed the target object signatures will be. For example, measuring L|pcs for both (i) the combination of closed-circuit cooperative sources 700 and 710 as well as (ii) the closed-circuit cooperative source 700 alone will yield a more detailed target object signature than simply measuring L|pcs for the closed-circuit cooperative source 700 alone. Similarly, measuring L|pcs with a third combination of closed-circuit cooperative sources 705 and 715, in addition to the previous two configurations, will yield an even more detailed target object signature. As one skilled in the art will appreciate, any number of cooperative sources may be implemented in the cooperative source array. Moreover, any number of combinations of closed-circuit cooperative sources may be measured to yield the desired level of detail for the target object signature.

Figure 8:
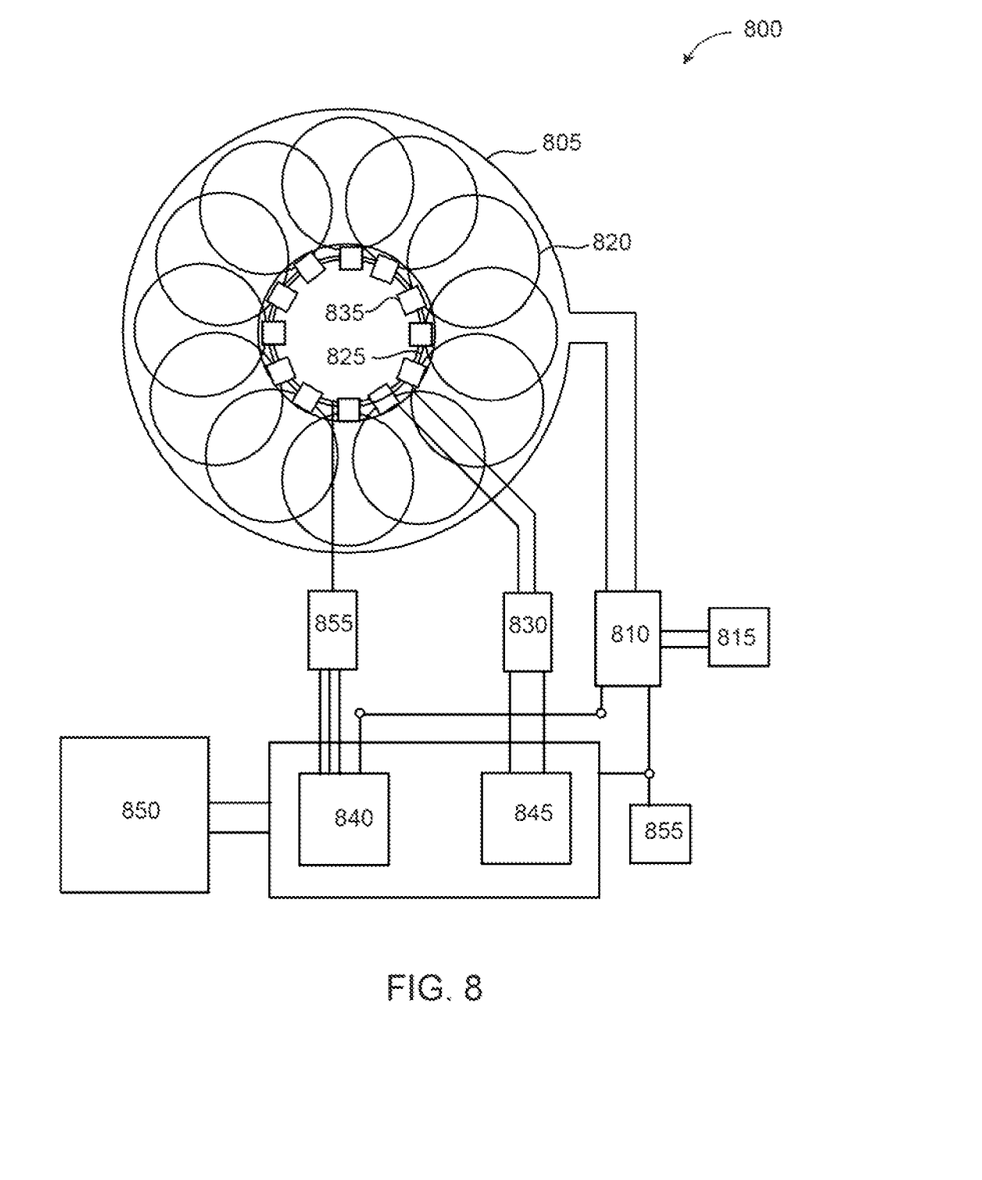
FIG. 8 illustrates a cooperative source EMI sensing device utilizing a cooperative source array in accordance with an embodiment of the disclosure.

Referring to FIG. 8, in a further embodiment, a cooperative source array is shown implemented as an EMI cooperative source time-domain sensor 800. A multi-turn transmitter coil 805 is energized by a software-configurable bipolar square wave. The transmitter waveforms are synthesized via an h-bridge switching configuration controlled by a pulse-switch modulator 810. An independent direct current power supply 815 is used to energize the transmitter. Decay of the induced currents from target objects as well as the closed-circuited cooperative sources 820 give rise to an EMI response (which can be measured as a voltage difference) in the multi-turn, air-core receiver coil 825. The receiver signals are amplified and filtered (e.g., within module 830) before analog-to-digital conversion. The cooperative sources 820 include local switch controls 855, which can be toggled between open-circuit and closed-circuit configurations using a digitally-controlled switchbox 840. In one or more embodiments, digital control of local switch controls 855 via digitally-controlled switchbox 840 and digital-to-analog conversion 845 are performed using a multi-function data acquisition board which is controlled by a field computer 850, such as presented in FIG. 9, described below. Also, in one or more embodiments, timing and triggering signals are generated using a stable quartz clock circuitry 855.

It is further understood that the EMI cooperative source sensing device 800 may be configured to automatically open and close any combination of the cooperative sources 820 and take inductive measurements. The benefits of such automation allow for multiple configurations of cooperative sources to be measured much more quickly than would be possible by manually opening and closing the switching circuits.

The inductive responses (i.e., L|pcs, L|p, L|cs, L|bg) recorded in all embodiments may be interpreted using statistical classification software. For example self-organizing map (SOM) software may be used. SOMs are computational (or artificial) neural networks that are well-suited for solving unsupervised classification problems. A trained SOM projects, onto a small regular two-dimensional grid or map, the most significant correlations that are inherent in a suite of high-dimensional input vectors. The SOM in this way provides efficient information compression while preserving important relationships amongst the various input vectors. The SOM software operates in two modes: training and classification. As one skilled in the art will appreciate, the training mode may be used to build maps using examples gathered by experimentation with the cooperative source device in a controlled environment.

More specifically, merge self-organizing maps (MSOM) may be used for general clustering and classification but also to discriminate target objects. The MSOM technique is specifically designed for spatiotemporal datasets. At a given time step, the MSOM codes additional information about the values of the input dataset from those of the previous time step. Thus, both spatial and temporal data correlations are projected onto the map. The use of MSOM for target classification based on conventional spatiotemporal inductive response datasets is known in the art.

The classification software may also be built into the cooperative source device, with classification results displayed on a console in an intuitive fashion so that the device can be operated by a person with little prior training. The software may analyze measured inductive responses in near real-time, allowing for the operator to classify and discriminate a target object while the EMI sensing device remains situated over the target object.

The cooperative source device may also be deployed in a hand-held mode or mounted to a mobile platform with wheels or tracks, both of which allow the device to traverse rugged terrain and maneuver within confined spaces. Such embodiments would allow the device to be used on a wide range of landscapes and vegetation cover, providing a reliable standard for classifying and discriminating unexploded ordnance and other target objects of interest.

The above described figure generally represents a device for classifying (i.e., enabling identification of a type and shape of) and discriminating (i.e., enabling identification of more specific characteristics of) an unknown target object utilizing a cooperative source within a cooperative source electromagnetic induction (EMI) sensing system. According to one aspect, the device includes: a transmitter configured to generate a time-varying primary magnetic field in the vicinity of the target object, which time-varying primary magnetic field inductively couples with the target object to generate a target object secondary magnetic field; and at least one cooperative source to which the primary magnetic field is also inductively coupled, generating one or more respective cooperative source secondary magnetic fields. The target object and the at least one cooperative source are inductively coupled via the target object secondary magnetic field and the one or more cooperative source secondary magnetic fields. The device further includes a receiver configured to measure a composite inductive response, which comprises a measurement of the inductive coupling of the target object and the one or more cooperative sources. According to one embodiment, the device further includes and/or is communicatively coupled to a data processor executing statistical classifier software that is configured for: interpreting a signature of the target object based upon the measured composite inductive response; and identifying the target object from the interpreted signature.

In one or more embodiments, one or more of the at least one cooperative source is a circuit and is configured to be switchable between an open-circuit and a closed-circuit configuration. Further, the device includes a switchbox configured to control the opening and closing of the cooperative source circuit. In at least one embodiment, the at least one cooperative source is a cooperative source array comprising a plurality of cooperative sources positioned at different locations and orientations relative to the target object and which can each be selectively activated and deactivated (individually or in tandem with one or more other cooperative sources) to yield different inductive responses.

Figure 9:
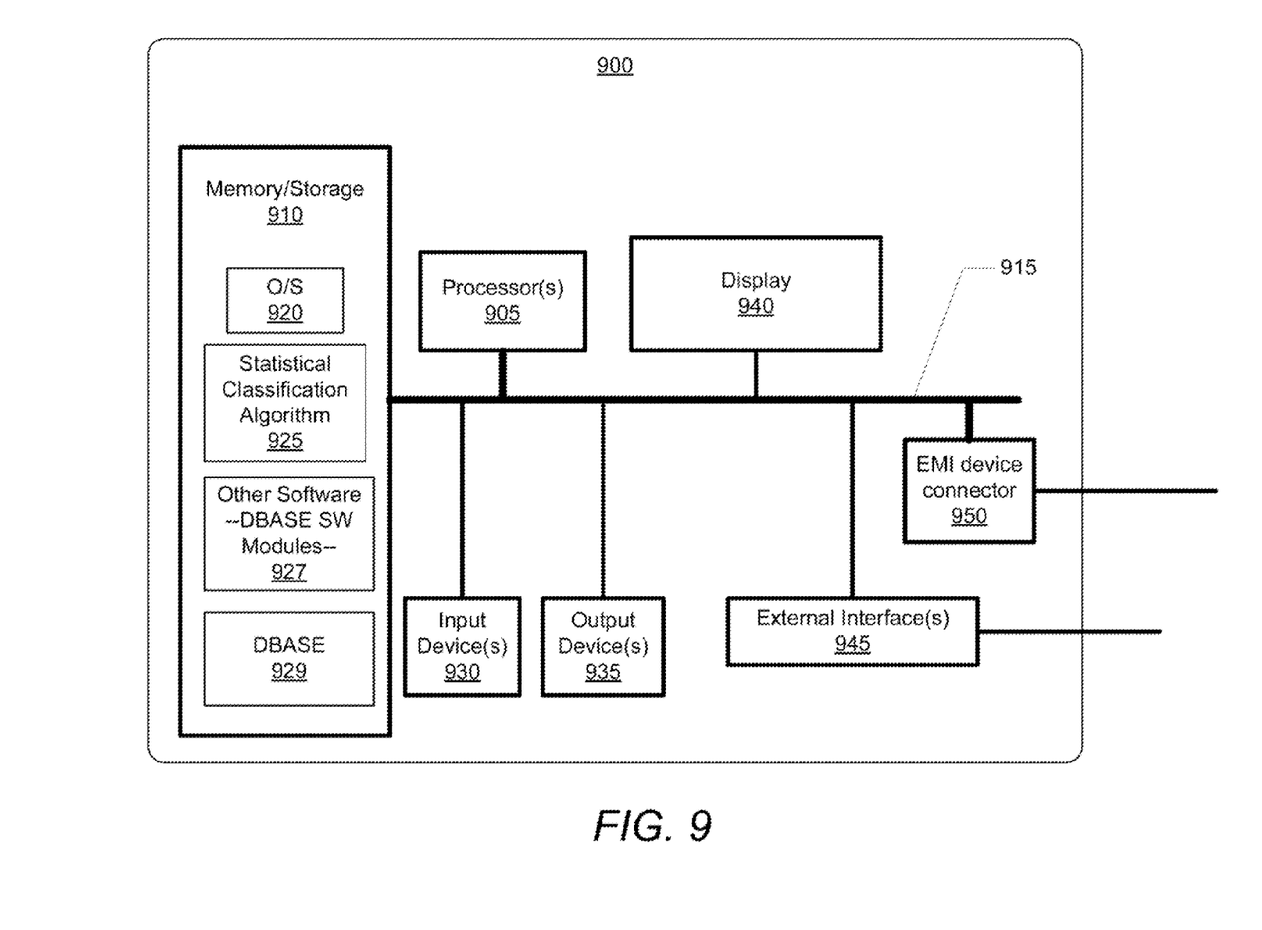
FIG. 9 illustrate components of an example data processing device that provides the EMI signal analyses and target identification processes, according to one or more embodiment.

Finally, in one embodiment, and as presented by FIG. 9, the device further includes and/or is communicatively connected to a data processing device (e.g., field computer 850 in FIG. 8) having statistical classifier software executing on the data processing device. The statistical classifier software is configured for: interpreting a signature of the target object based upon the measured composite inductive response; and identifying the target object from the interpreted signature. The statistical classifier software utilizes at least one of (a) self-organizing maps and (b) merge self-organizing maps.

As shown by FIG. 9, example data processing device 900, which can be utilized as field computer 850 (FIG. 8) includes processor(s) 905 which is coupled to memory/storage 910 via a system interconnect 915. Memory/storage 910 includes operating system (OS) 920 and statistical classification algorithm 925, which executes on processor(s) 905 to generate or perform specific functions as described herein. Also connected via system interconnect 915 are one or more input devices 930, and one or more output devices 935, of which display 940 is provided as a separate device. Data processing device 900 can also include external interface(s) 945 for connecting to one or more secondary devices or systems, of which a network such as the Internet and additional storage, are possible examples. Data processing device 900 also includes an EMI device connector 950 which generally represents the mechanism by which the data processing device 900 connects to and communicates with cooperative source EMI device 800. It is appreciated that the connection can be wired or wireless, and the data processing system 900 can be local to the cooperative source EMI device 800 (e.g., on a same physical structure) or remote from the cooperative source EMI device 800, in alternate embodiments.

According to one or more embodiments, the EMI device connector 950 can be a universal serial bus (USB), peripheral component interconnect (PCI) or Personal Computer Memory Card International Association (PCMCIA) port depending on the design of the system. In general, the data processing system is a field PC or tablet that interfaces with a multi-function DAQ card. Control and data acquisition is performed via digital and analog ports of the data acquisition (DAQ) card. With this embodiment, there can be four software layers above the OS 920, including (i) DAQ card drivers, (ii) a run-time engine which allows or enables .exe real time DAQ software to run, (iii) I/O control and pre-processing software and (iv) a database training and classification software that can be run in real-time after the software has been trained. These various software components are generally represented by other software or database software modules 927, which collectively enable collection of target data and/or updates and/or maintain target object database 929. In one embodiment, statistical classification algorithm 925 accesses database 929 and particularly the target signatures stored therein to perform the analyses and matching of detected signature with target signatures of known targets recorded within database 929.

Figure 10:
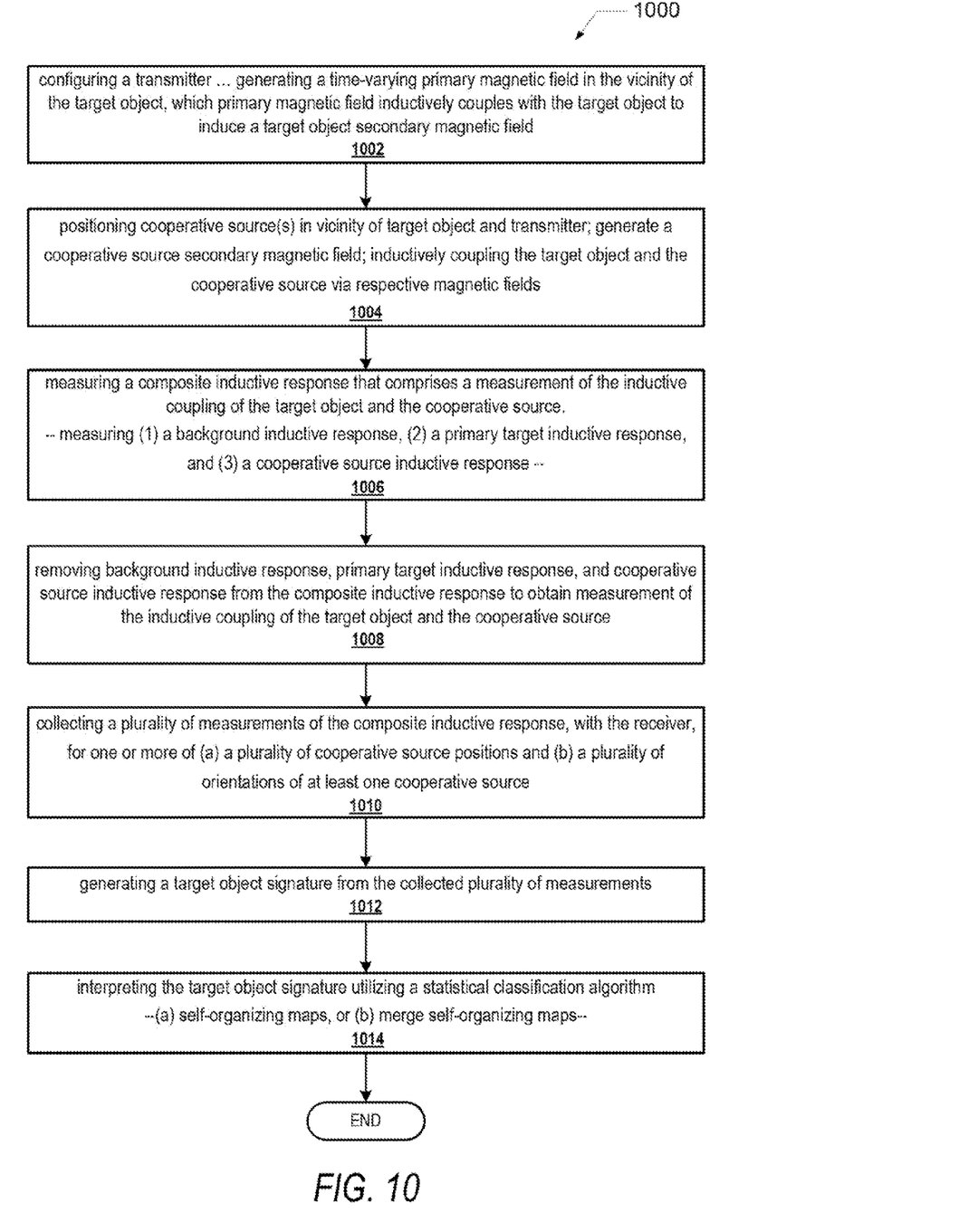
FIG. 10 is a flow chart of a method by which the EMI sensing system operates to identify a target object using one or more cooperative source(s), according to one embodiment.

Turning now to FIG. 10, there is illustrated a flow chart representing an example method by which the various aspects of the above measurements and analyses of EMI data and/or signals can be implemented, in one or more embodiments. Certain aspects of the method are provided by control mechanisms of the above described EMI sensing device of FIGS. 3, 4, 7, and 8, while other aspects can be provided by the data processing device of FIG. 9 and particularly processor execution of specific code within the data processing device. For simplicity, method 1000 is described generally, without specific reference to a particular component, for the most part. Each functional aspect of the method is presented in a separate block, and in some instances multiple related or corresponding functions are presented in the same block. According to the presented embodiment, method 1000 includes: generating a time-varying primary magnetic field in the vicinity of the target object, which primary magnetic field inductively couples with the target object to induce a target object secondary magnetic field (block 1002). Notably, as also presented within block 1002, the generating function can include configuring a transmitter of an electromagnetic induction (EMI) sensing device to perform the generating.

Method 1000 further includes positioning at least one cooperative source in the vicinity of the target object and the transmitter, where an inductive coupling of the primary magnetic field with the at least one cooperative source generates a cooperative source secondary magnetic field (block 1004). As an extension of this function, the target object and the cooperative source are inductively coupled via the target object secondary magnetic field and the cooperative source secondary magnetic field. Method 1000 further includes measuring, with a receiver, a composite inductive response that comprises a measurement of the inductive coupling of the target object and the cooperative source (block 1006). The receiver is a component of the EMI sensing device. Notably, this measuring process further includes measuring a background inductive response, a primary target inductive response, and a cooperative source inductive response (block 1006). Method 1000 then provides removing the background inductive response, the primary target inductive response, and the cooperative source inductive response from the composite inductive response to yield/obtain the measurement of the inductive coupling of the target object and the cooperative source (block 1008).

As provided at block 1010, method 1000 further includes: collecting a plurality of measurements of the composite inductive response, with the receiver, for one or more of (a) a plurality of cooperative source positions and (b) a plurality of orientations of at least one cooperative source. Method 1000 also provides generating a target object signature from the collected plurality of measurements (block 1012) and interpreting the target object signature utilizing a statistical classification algorithm (block 1014). The statistical classification algorithm utilizes one or more layers of (a) self-organizing maps and/or (b) merge self-organizing maps or (c) combinations of both. In at least one embodiment, the at least one cooperative source is a cooperative source array comprising a plurality of cooperative sources positioned at different locations and orientations relative to the target object and which can each be selectively activated and deactivated (individually or in tandem with one or more other cooperative sources) to yield different inductive responses. Method 1000 then terminates at the end block.

The processes disclosed above may be in the form of a computer program product accessible from a computer-usable or computer-readable medium providing program code for use by or in connection with a computer or any other instruction execution system. For the purposes of this description, a computer-usable or computer readable medium can be any tangible apparatus that can contain, store, communicate, propagate, or transport the program for use by or in connection with the instruction execution system or device.

The medium can be an electronic, magnetic, optical, electromagnetic, infrared, or semiconductor system or device or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) Digital Video/Versatile Disk (DVD) etc.

While the disclosure has been described with reference to exemplary embodiments, it will be understood by those skilled in the art that various changes may be made and equivalents may be substituted for elements thereof without departing from the scope of the disclosure. In addition, many modifications may be made to adapt a particular system, device or component thereof to the teachings of the disclosure without departing from the essential scope thereof. Therefore, it is intended that the disclosure not be limited to the particular embodiments disclosed for carrying out this disclosure, but that the disclosure will include all embodiments falling within the scope of the appended claims. Moreover, the use of the terms first, second, etc. do not denote any order or importance, but rather the terms first, second, etc. are used to distinguish one element from another.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present disclosure has been presented for purposes of illustration and description, but is not intended to be exhaustive or limited to the disclosure in the form disclosed. Many modifications and variations will be apparent to those of ordinary skill in the art without departing from the scope of the disclosure. The described embodiments were chosen and described in order to best explain the principles of the disclosure and the practical application, and to enable others of ordinary skill in the art to understand the disclosure for various embodiments with various modifications as are suited to the particular use contemplated.

It is to be understood that the above description and examples are intended to be illustrative, and not restrictive. For example, the above-described embodiments may be used in combination with each other. Many other embodiments will be apparent to those of skill in the art upon reviewing the above description. The scope of the disclosure therefore should be determined with reference to the appended claims, along with the full scope of equivalents to which such claims are entitled.

What is claimed is:

1. A device for classifying and discriminating an unknown target object, the device comprising:
   a transmitter configured to generate a time-varying primary magnetic field in the vicinity of the target object, which time-varying primary magnetic field inductively couples with the target object to generate a target object secondary magnetic field;
   at least one cooperative source to which the primary magnetic field is also inductively coupled, generating one or more respective cooperative source secondary magnetic fields, wherein the target object and the at least one cooperative source are inductively coupled via the target object secondary magnetic field and the one or more cooperative source secondary magnetic fields; and
   a receiver configured to measure a composite inductive response, which comprises a measurement of the inductive coupling of the target object and the one or more cooperative sources.

2. The device of claim 1, wherein the cooperative source comprises a metal object that couples inductively to a time-varying magnetic field.

3. The device of claim 1, wherein one or more of the at least one cooperative source is a circuit and is configured to be switchable between an open-circuit and a closed-circuit configuration.

4. The device of claim 3, further comprising a switchbox configured to control the opening and closing of the cooperative source circuit.

5. The device of claim 1, further comprising a data processing device and statistical classifier software executing on the data processing device and configured for: interpreting a signature of the target object based upon the measured composite inductive response; and identifying the target object from the interpreted signature.

6. The device of claim 5, wherein the statistical classifier software utilizes self-organizing maps.

7. The device of claim 6, wherein the statistical classifier software utilizes merge self-organizing maps.

8. The device of claim 1, wherein the at least one cooperative source is a cooperative source array comprising a plurality of cooperative sources positioned at different locations and orientations relative to the target object and which can each be selectively activated and deactivated, either individually or in tandem with other cooperative sources, to yield different inductive responses.

9. A method for classifying and discriminating a target object, the method comprising:
   generating a time-varying primary magnetic field in the vicinity of the target object, which primary magnetic field inductively couples with the target object to induce a target object secondary magnetic field;
   positioning at least one cooperative source in the vicinity of the target object and the transmitter, where an inductive coupling of the primary magnetic field with the at least one cooperative source generates a cooperative source secondary magnetic field, and wherein the target object and the cooperative source are inductively coupled via the target object secondary magnetic field and the cooperative source secondary magnetic field; and
   measuring, with a receiver, a composite inductive response that comprises a measurement of the inductive coupling of the target object and the cooperative source.

10. The method of claim 9, wherein generating comprises configuring a transmitter of an electromagnetic induction (EMI) sensing device to perform the generating and wherein the receiver is a component of the EMI sensing device.

11. The method of claim 9, further comprising measuring, with the receiver, a background inductive response.

12. The method of claim 11, further comprising measuring, with the receiver, a primary target inductive response.

13. The method of claim 12, further comprising measuring, with the receiver, a cooperative source inductive response.

14. The method of claim 13, further comprising removing the background inductive response, the primary target inductive response, and the cooperative source inductive response from the composite inductive response to yield the measurement of the inductive coupling of the target object and the cooperative source.

15. The method of claim 14, further comprising collecting a plurality of measurements of the composite inductive response, with the receiver, for one or more of (a) a plurality of cooperative source positions and (b) a plurality of orientations of at least one cooperative source.

16. The method of claim 15, further comprising generating a target object signature from the collected plurality of measurements.

17. The method of claim 16, further comprising interpreting the target object signature utilizing a statistical classification algorithm.

18. The method of claim 17, wherein the statistical classification algorithm utilizes self-organizing maps.

19. The method of claim 17, wherein the statistical classification algorithm utilizes merge self-organizing maps.

20. The method of claim 9, wherein the at least one cooperative source is a cooperative source array comprising a plurality of cooperative sources positioned at different locations and orientations relative to the target object and which can each be selectively activated and deactivated, either individually or in tandem with other cooperative sources, to yield different inductive responses.

* * * * *